350-96.26 SR
2/3/81 XR 4,248,213

United States Patent [19]
Landre

[11] 4,248,213
[45] Feb. 3, 1981

[54] ARTICULATED OPTICAL COUPLER

[75] Inventor: John K. Landré, La Honda, Calif.
[73] Assignee: Syn-Optics, Sunnyvale, Calif.

[21] Appl. No.: 66,266
[22] Filed: Aug. 13, 1979
[51] Int. Cl.[3] .................... A61B 1/06
[52] U.S. Cl. .................... 128/6; 350/96.26; 358/98
[58] Field of Search .................... 128/6, 4, 7-9; 350/96.26; 358/98

[56] References Cited

U.S. PATENT DOCUMENTS 4,074,306 2/1978 Kakinoma et al. .................. 128/6 X

*Primary Examiner*—John D. Yasko
*Attorney, Agent, or Firm*—Townsend and Townsend

[57] ABSTRACT

An articulated coupler which, when inserted between an endoscope and a suspended television camera, allows all rotations of the endoscope to occur while automatically avoiding image rotation on the television screen. The coupler includes first and second right angle deflectors, first and second rotatable bearings, and a compensation mechanism. Light is incident along a first optical axis (endoscope axis) and ultimately emerges along a second optical axis (camera axis). The first rotatable bearing is disposed between the first and second deflectors to permit relative rotation of the first and second deflectors about the coupler optical axis (horizontal). The second rotatable bearing is disposed between the second deflector and the camera to permit relative rotation of the second deflector and the camera about the camera optical axis. The compensation mechanism rotates the camera about the camera optical axis relative to the second deflector in an amount and direction necessary to compensate for the relative rotation between the first and second deflectors about the coupler optical axis that arises from pitch rotation of the endoscope. The compensation mechanism preferably comprises first and second bevel gears coaxial with the coupler optical axis and the camera optical axis, respectively, which gears are rigidly coupled to the first deflector and to the television camera, respectively, and are carried coaxially on mutually perpendicular hollow sleeve bearings that are rigidly coupled to the second deflector. In an embodiment where the gears mesh directly, the second deflector is configured to cause an even number of reflections.

16 Claims, 3 Drawing Figures

ARTICULATED OPTICAL COUPLER

FIELD OF THE INVENTION

The present invention relates to an optical coupler between a first optical system that is free to rotate in three dimensions and a second optical system that is free to rotate only about its optical axis, such as an optical coupler between a endoscope and a suspended television camera.

BACKGROUND OF THE INVENTION

An endoscope is an optical instrument for viewing and examining the interior of an organ within the human body. Broadly, an endoscope comprises a long thin tube within which are housed fiber optic elements for transmitting light to the interior regions to be viewed, and image forming and relay optical elements for transmitting an optical image to an eyepiece outside the body for viewing by the examining physician. In use, the endoscope is typically oriented with its axis pointing in a generally horizontal direction, and the physician wiggles it around to view different interior portions.

It is desirable in many circumstances to have the optical image from the endoscope fed to a television camera for viewing by more than one person or for video recording thereof. Currently, tube type television cameras are the only type in widespread use. However, even when the head of a tube type television camera is separated from the remaining portions, it represents a sizeable weight. Thus, it is not practical to directly couple a television camera to a rigid endoscope disposed within a patient without providing some sort of support mechanism for the camera.

It is known to suspend a television camera head by a cable from a pulley or a microphone boom. The camera head represents a cylindrical body, generally symmetric about its optical axis. Accordingly, the camera is suspended pointing downward (optical axis vertical) and an optical coupler between the generally horizontal endoscope and the camera must be provided. The coupler typically includes a beam splitter for simultaneous direct and television viewing. A camera relay tube is also normally used to keep the camera (which cannot be sterilized) as far from the sterile field as possible.

Even if it is possible to insert the endoscope into the patient horizontally, it is generally required that rotations and translations in three dimensions be made in the course of examination. Rotations arise as the physician moves the eyepiece end of the endoscope, so that the endoscope pivots about a point generally defined by surrounding body tissue. These rotations include rotations about the endoscope's own axis (hereinafter roll axis), rotations about a horizontal axis perpendicular to the endoscope axis (hereinafter pitch axis), and rotations about an axis perpendicular to the pitch and roll axes (hereinafter yaw axis). If a rigid coupler with a deflection mirror is used, it can be appreciated that the endoscope may be translated vertically, and may be translated horizontally so long as the angle of the suspension cable with respect to the vertical remains small. Additionally, the endoscope may be rotated about the suspension cable without placing any of the camera weight on the eyepiece end of the endoscope. However, it is impossible to rotate the endoscope about the pitch and roll axes.

Roll rotation of the endoscope is typically accommodated by providing the coupler with a bearing between the endoscope and the deflection mirror. Additionally, rotation about the pitch axis may be provided by adding a second mirror to the coupler. The first mirror is placed to produce a 90° deflection about an axis parallel to the yaw axis so that light emerges horizontally parallel to the pitch axis, thus defining a coupler optical axis. The second mirror is placed to provide a 90° vertical deflection to the television camera. A bearing between the two mirrors accommodates relative rotation about the coupler optical axis.

Unfortunately, the type of coupler described above results in undesirable image rotation when the endoscope is rotated in such a manner that the first mirror rotates relative to the second. That is, as the examining physician manipulates the endoscope to scan different portions of the organ being viewed, rotation of the endoscope about the pitch axis causes the image on the television screen to rotate. The standard way of handling such image rotation is the placement of a rotatable Dove prism in the camera relay system between the coupler and the television camera. Since rotation of the Dove prism causes a rotation of the image seen on the television screen, image rotation may be at least partly compensated by having an operator view the television monitor and appropriately rotate the prism. This system is still far from optimal, since even the most experienced operator is unable to completely eliminate disconcerting image rotation. Moreover, the required presence of a second person within the sterile field in close proximity to the examining physician is inconvenient at best, hazardous at worst.

Accordingly, when it is required to provide television viewing of the results of endoscopic examination procedures where the examining physician has to rotate the endoscope about all three axes, the choice has been between having an extra operator immediately nearby or putting up with disconcerting image rotation on the television screen.

SUMMARY OF THE INVENTION

The apparatus of the present invention is an articulated coupler which, when inserted between an endoscope and a suspended television camera, allows all rotations of the endoscope to occur while automatically avoiding image rotation on the television screen.

Broadly, a coupler according to the present invention includes first and second right angle deflectors, first and second rotatable bearings, and a compensation mechanism. Light is incident along a first optical axis (endoscope axis) and ultimately emerges along a second optical axis (camera axis). The first deflector deflects light travelling along the endoscope optical axis about the yaw axis so that it emerges along a third optical axis, designated the coupler optical axis, that is parallel to the pitch axis. The second deflector deflects that light travelling along the coupler optical axis vertically upwardly so that it emerges along the camera optical axis. The first rotatable bearing is disposed between the first and second deflectors to permit relative rotation of the first and second deflectors about the coupler optical axis. The second rotatable bearing is disposed between the second deflector and the camera to permit relative rotation of the second deflector and the camera about the camera optical axis. A third bearing is typically provided between the endoscope eyepiece and the first deflector to accommodate roll rotation of the endoscope. The compensation mechanism has the function of rotating the camera about the camera optical axis relative to the second deflector in an amount and direction necessary to compensate for the relative rotation between the first and second deflectors about the coupler optical axis that arises from pitch rotation of the endoscope. In this context, the term "camera" should also be taken to include the camera relay tube, where such a relay tube is used. Moreover, the term "camera" is sometimes used to refer to the camera head.

The compensation mechanism preferably comprises first and second bevel gears coaxial with the coupler optical axis and the camera optical axis, respectively, which gears are rigidly coupled to the first deflector and to the television camera, respectively, and are carried coaxially on hollow sleeve bearings at right angles to one another. The hollow sleeve bearings are both rigidly coupled to the second deflector. Each bevel gear, together with the sleeve bearing on which it is carried, defines one of the rotatable bearings.

In a first embodiment, the gears mesh directly, in which case it is necessary that the second deflector cause an even number of reflections. This may be most easily accomplished with paired reflective surfaces at 45° to one another and having respective normals lying in the plane defined by the coupler and camera optical axes. The reflective surfaces may be carried on separate mirrors, or may be part of a pentaprism. When the second deflector causes an even number of reflections, it is desirable that the first deflector also cause an even number of reflections so that the image relayed to the television camera has the same handedness or parity as the viewed image.

In a second embodiment, an idler gear is interposed between the first and second bevel gears, in which case it is necessary that the second deflector cause an odd number of reflections. This is most easily accomplished by a single relective surface at 45° to the coupler and camera optical axes. In order to maintain parity, the first deflector should also cause an odd number of reflections.

For a further understanding of the nature and advantages of the present invention, reference should be had to the remaining portions of this specification and to the attached drawings.

DETAILED DESCRIPTION OF THE INVENTION

Figure 1:
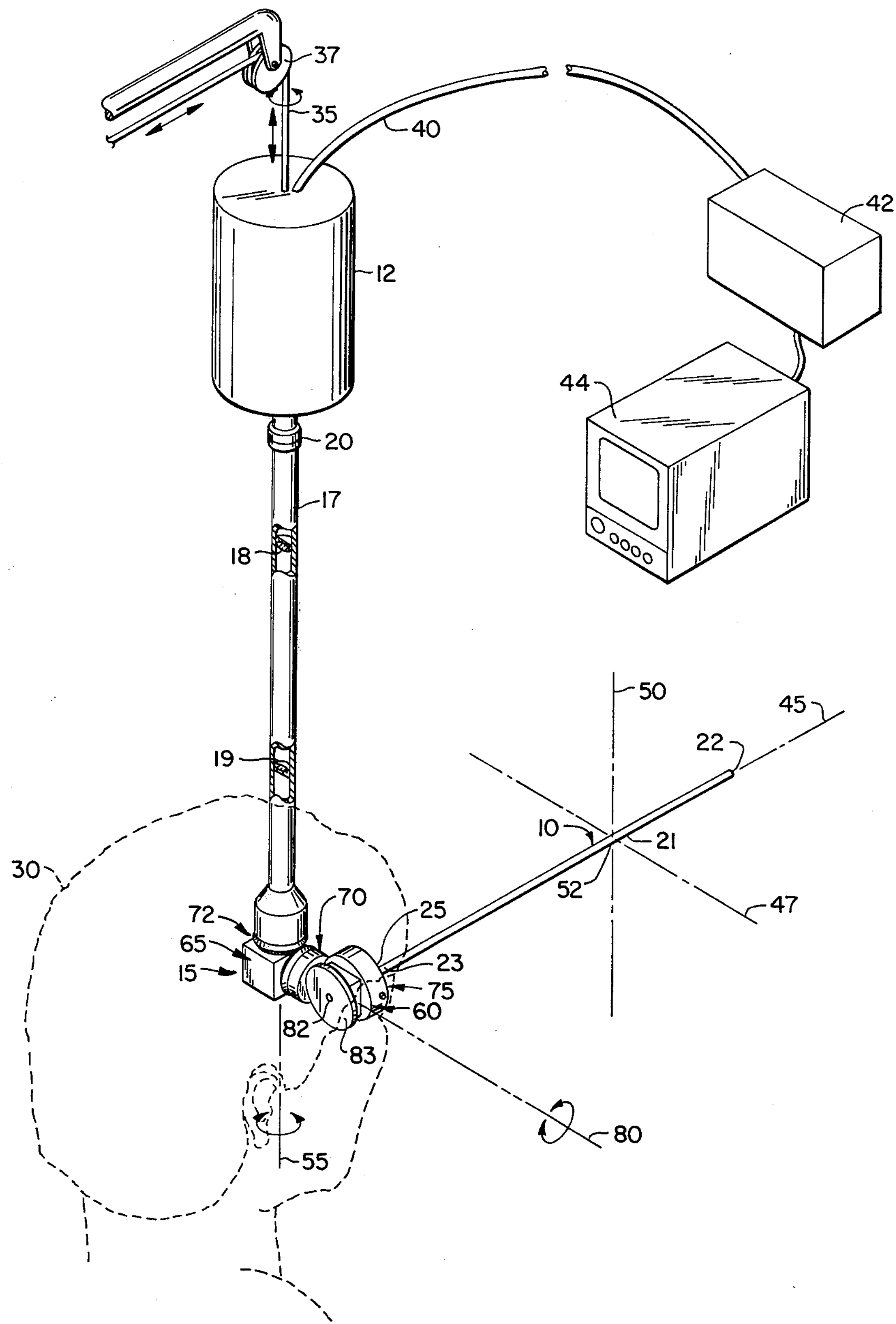
FIG. 1 is an isometric schematic view of the coupler inserted between an endoscope and a suspended television camera.

FIG. 1 is a schematic view showing the transmission of optical information from a rigid endoscope 10 to a suspended television camera head 12 (hereinafter sometimes "cameras" for short) through an articulated optical coupler 15. Camera 12 is spaced above coupler 15 by a relay tube 17 within which are located symmetric relay lenses 18 and 19. A quick disconnect coupling 20 near the upper end of relay tube 17 allows for easy hookup after coupler 15 and endoscope 10 have been sterilized. Endoscope 10 includes a thin rigid tube 21 having a first distal end 22 for insertion into a body cavity or organ of a patient and a proximal end 23 to which is affixed an eyepiece 25. Within tube 21 are light transmitting fibers to illuminate the interior body region being viewed, and optical elements for forming and relaying an image to the eyepiece for viewing by an examing physician 30. Television camera head 12 is suspended by a cable 35 from a pully 37, suitable counterweights eliminating any weight of camera head 12 and coupler 15 on endoscope 10 while allowing vertical movement and rotation. A microphone boom may also be used for a balanced suspension. Head 12 communicates via a signal carrying cable 40 to remaining portions 42 of the camera for providing a video signal which may be viewed on a television monitor 44. Endoscope 10 and television camera 12 are standard articles of manufacture, and since they form no part of the invention, they will not be described in further detail.

The orientation of endoscope 10 is characterized by rotational displacements about a roll axis 45 generally corresponding to the endoscope optical axis, a pitch axis 47 perpendicular to roll axis 45, and a mutually perpendicular yaw axis 50. While endoscope 10 is maintained in a generally horizontal position, the physician must be free to manipulate the endoscope so that it undergoes rotation about all three axes. These rotations arise as the physician moves proximal end 23 of the endoscope which pivots about a pivot point 52 defined by surrounding body tissue.

The orientation of camera 12 is characterized by a camera optical axis 55 that is preferably maintained substantially vertical by the suspension system described above. The purpose of coupler 15 is to permit endoscope 10 to be rotated about all three axes while camera head 12 undergoes rotation only about axis 55.

Broadly, coupler 15 includes a first deflector 60, a second deflector 65, a first bearing 70 for accommodating relative rotation between deflectors 60 and 65, a second bearing 72 for accommodating relative rotation between camera relay tube 17 (and camera head 12 therewith) and second deflector 65, and a third bearing 75 for accommodating relative rotation between endoscope 10 and first deflector 60.

First deflector 60 provides a right angle deflection so that light travelling along endoscope axis 45 is deflected to emerge horizontally along a coupler optical axis 80 that is horizontal and parallel to pitch axis 47. Second deflector 65 causes light travelling along coupler axis 80 to be deflected perpendicularly so that it travels upwardly along camera optical axis 55. First deflector 60 preferably contains a beam splitter to permit direct viewing by physician 30 through an aperture 82 centered on an eyepiece ring 83.

Figure 2:
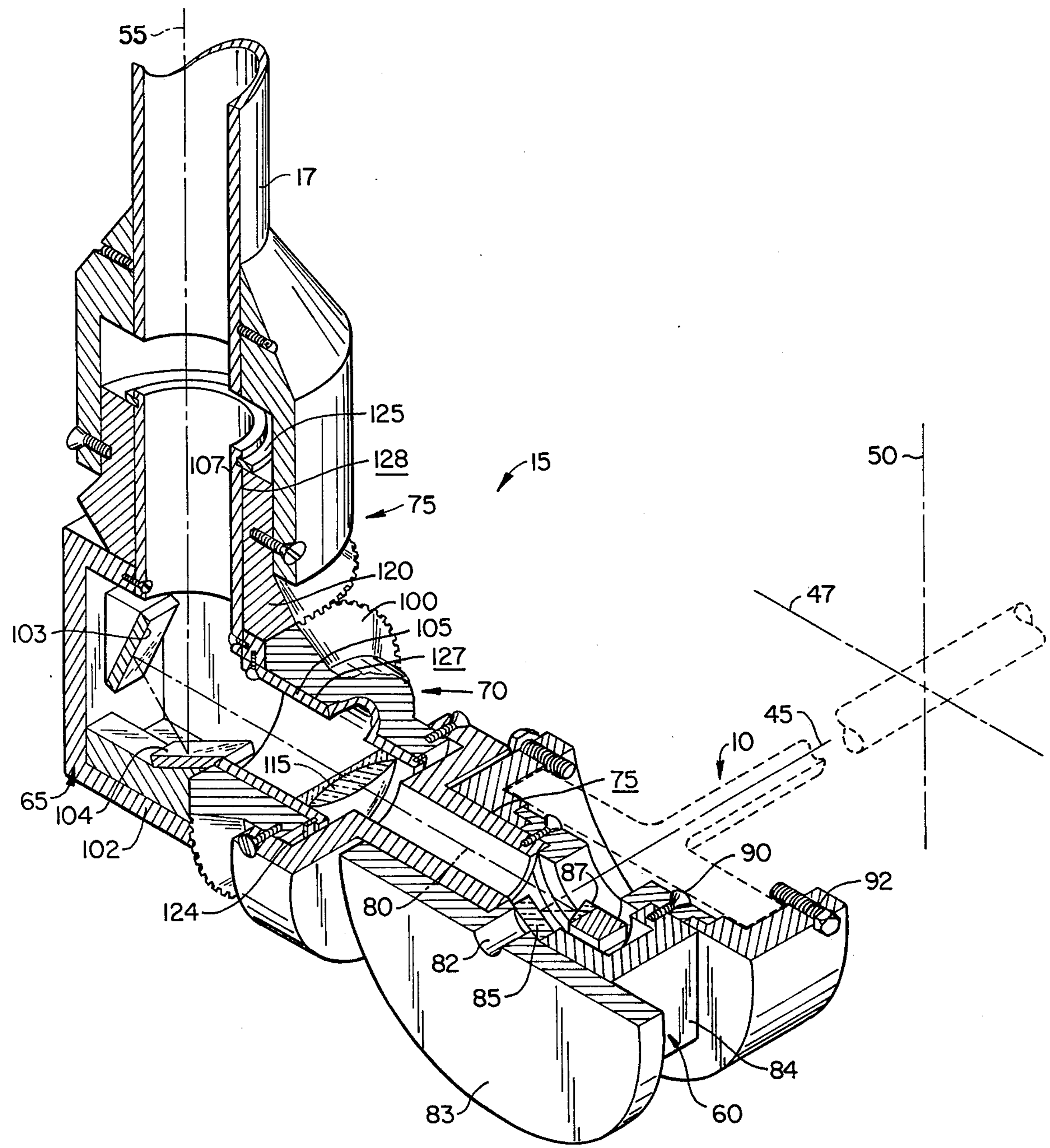
FIG. 2 is an isometric sectional view showing the detailed construction of the coupler.

FIG. 2 is a sectional isometric view showing the detailed construction of a first embodiment of coupler 15. First deflector 60 comprises a housing 84 and first and second mirrors 85 and 87 mounted therein. Mirrors 85 and 87 are oriented at 45° with respect to one another and have their respective normals lying in the plane defined by endoscope optical axis 45 and coupler optical axis 80. The respective normals are preferably oriented symmetrically, namely at $22\frac{1}{2}°$ to axes 45 and 80. A flanged ring 90 rotatably retains an endoscope eyepiece clamp 92 to define bearing surface 75. Mirror 85 is only partially silvered so that a small fraction (approximately 20%) of the light incident on it from endoscope 10 is transmitted through aperture 82. First deflector housing 84 carries a first bevel gear 100 which is rigidly mounted thereto.

Second deflector 65 comprises a housing 102 and first and second plane mirrors 103 and 104 mounted therein. Second deflector housing 102 carries rigidly mounted mutually perpendicular first and second hollow sleeve bearings 105 and 107, ultimately aligned along the coupler optical axis and the camera optical axis, respectively. Mirrors 103 and 104 are in a configuration similar to that occupied by mirrors 85 and 87. An objective lens 115 is mounted along coupler optical axis 80 within hollow sleeve bearing 105 which also functions as a lens tube. Coaxial alignment is thus automatically achieved. Camera relay tube 17 has rigidly mounted thereto in a coaxial arrangement a second bevel gear 120. Bevel gears 100 and 120 are standard miter gears characterized by a cone half angle of 45°.

Bevel gears 100 and 120 have coaxial bores sized for rotatable mounting about hollow sleeve bearings 105 and 107 and are mounted thereon and maintained in engagement with one another by respective retaining rings 124 and 125 on the sleeve bearings. Gears 100 and 120 with sleeve bearings 105 and 107 thus mate along respective bearing surfaces 127 and 128 which define rotatable bearings 70 and 72, respectively.

The construction of the components described above involves certain dimensional considerations that are best understood in the context of the opertion of the device. In opertion, generally parallel bundles of rays corresponding to different object points being viewed at a given time emerge from endoscope eyepiece 25 within a cone centered about endoscope axis 45. A portion of this light is transmitted by mirror 85 for direct viewing through aperture 82, while the remaining portion is reflected by mirrors 85 and 87 for a net average 90° deflection to emerge with a central ray along coupler optical axis 80 in a direction toward second deflector 65. Objective lens 115 transforms the generally parallel bundles into convergent bundles which are deflected by mirrors 110 and 112 for a net average 90° reflection to emerge along camera optical axis 55. The converging bundles form a real image of the various object points within relay tube 17, and relay lenses 18 and 19 transmit the real image to camera head 12.

The dimension of first deflector housing 84 along endoscope axis 45 is preferably as small as possible so that the examining physician looking through aperture 82 is able to get his eye reasonably close to eyepiece 25 where the exit pupil is situated. Thus he is able to view substantially the whole image without having to move his eye transversely to pick up the various emerging parallel bundles.

Since the optical path between objective lens 115 and eyepiece 25 is relatively long, objective 115 is of relative large diameter (e.g. 12 mm.) to pick up substantially all the off axis bundles and thus avoid vignetting. The use of a relatively large diameter objective lens, dictated by the large optical path between the exit pupil and the objective has a further beneficial result in that the need for a field lens proximate the first deflector is avoided.

It will now be apparent how roll, pitch, and yaw rotation of endoscope 10 are accommodated by coupler 15. Roll rotation is taken up by bearing 75, since endoscope eyepiece clamp 92 may rotate about endoscope axis 45 relative to first deflector 60 and the remaining portions of coupler 15. Yaw rotation about axis 50 may be accommodated by rotating the entire assembly about camera axis 55, although when axis 50 is not generally vertical, some inclination of camera 12 may occur. Pitch rotation produces a relative rotation between deflector 60 and deflector 65, which rotation is taken up by rotatable bearing 70 defined by first bevel gear 100 and first sleeve bearing 105. However, the rotation of bevel gear 100 relative to sleeve bearing 105, causes a commensurate rotation of bevel gear 120 (and camera relay tube 17 and camera 12 therewith) about second sleeve bearing 107. It is this second rotation that has the important effect of eliminating image rotation that would otherwise appear on monitor 44. That is, the relative rotation between the two deflectors causes a roation of the image in space, but the bevel gears cause a rotation of camera 12 by an equal amount so that the projected image is substantially non-rotated. Thus, as endoscope 10 is moved about by the examining physician as he probes the interior regions being examined, the image that appears on the television screen, if initially set at the same orientation as that being viewed directly, maintains that orientation.

The sense of the image rotation caused by the relative rotation between the two deflectors, and thus the direction of the needed compensation, depends on the number of reflections that the light undergoes within second deflector 65. In particular, where an even number of reflections occur, as for example where two mirrors (103 and 104) are used, the direct gear drive illustrated provides the proper sense of compensatory rotation. That is, a gear train providing an odd number of gear interfaces compensates for relative rotation when the second deflector causes an even number of reflections to occur. (The same is true with odd and even reversed). In this context it should be noted that the term "even number" includes a deflection system where no reflections occur, as for example if the deflections occur due to refraction. It is to be noted that a pentaprism may be used, but it must be remembered that a pentaprism produces internal reflections and is functionally no different from the mirrors. The use of paired mirrors 85 and 87 within first deflector housing 84 is dictated by the desire that the overall image handedness (or parity) be maintained. More generally, this will be achieved if the total number of reflections caused by the system is even.

Figure 3:
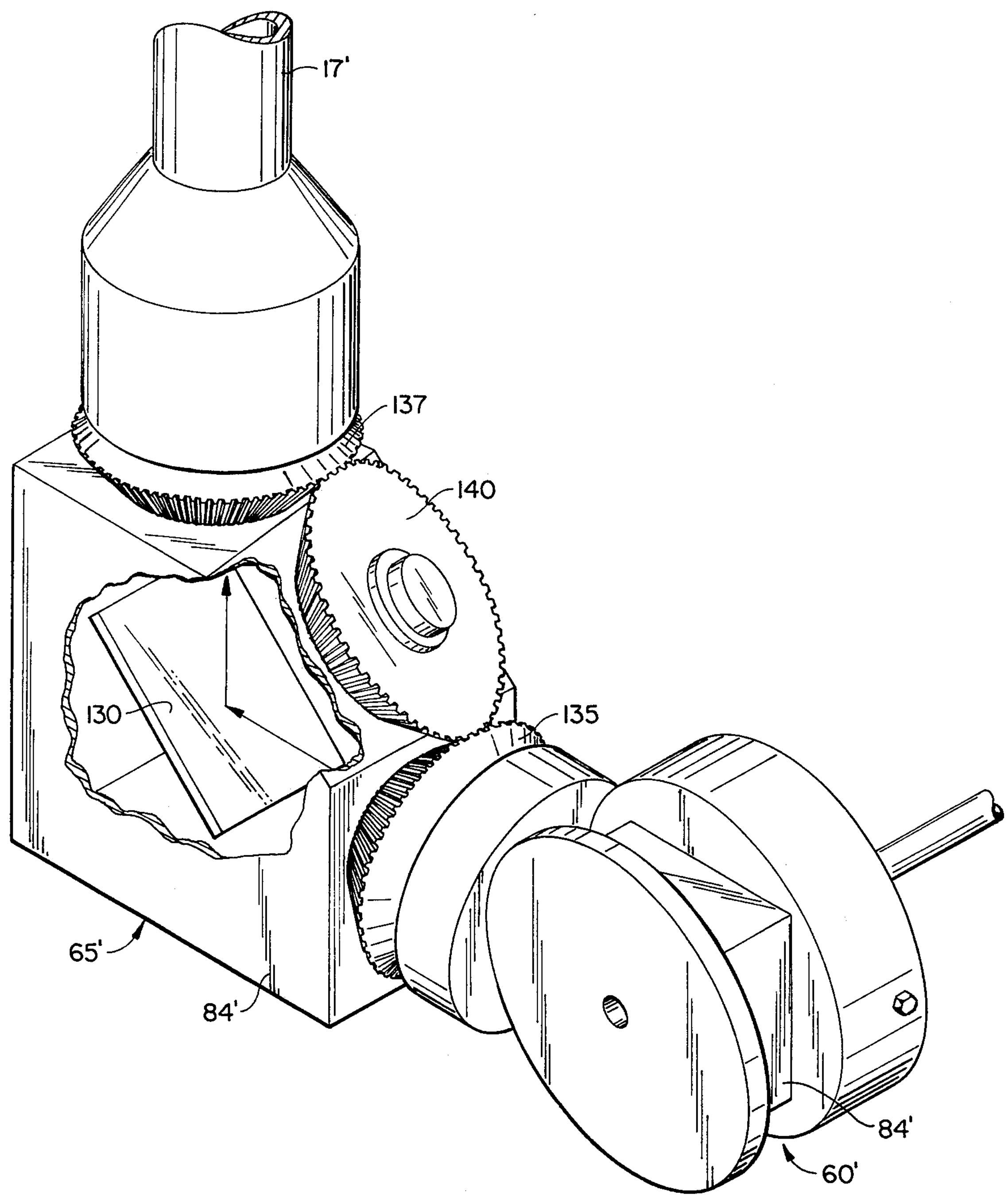
FIG. 3 is an isometric cutaway view of an alternate embodiment of the coupler.

FIG. 3 is a cutaway isometric view of a second embodiment of the present invention, elements corresponding to those of FIG. 2 being denoted by primed reference numerals. In this second embodiment, second deflector 65' comprises housing 84' within which is mounted a single reflector 130 oriented at 45° to both coupler axis 80 and camera axis 55. As noted above, the provision of a deflector that causes an odd number of reflections necessitates a gear drive providing an even number of gear interfaces. Therefore, first deflector housing 84' has rigidly mounted thereto a first bevel gear 135; relay tube 17' has rigidly mounted thereto a second bevel gear 137, bevel gears 135 and 137 being rotatably mounted to second deflector housing 84' with their axes perpendicular as in the first embodiment. However, bevel gears 135 and 137 do not engage each other directly, but rather both engage a third bevel gear 140 rotatably mounted to second deflector housing 84' with its axis at 45° to the axes of gears 135 and 137. The interposition of bevel gear 140 which functions as an idler requires that the three bevel gears have half cone angles of 22½° rather than 45° as in the case of gears 100 and 120 of FIG. 2.

In summary it can be seen that the present invention provides an optical coupler for use with a balanced camera suspension that is capable of taking up all rotations of the endoscope. The weight of the camera is fully compensated under all rotations and the image on the television screen does not rotate as the endoscope is moved freely in space. Thus, in use, a focusing and image rotation adjustment is made initially during installation (by rotating camera 12 relative to relay tube 17 prior to clamping it rigidly) and thereafter the image appears upright on the screen.

While the above provides a full and complete disclosure of the preferred embodiments of the present invention, various modifications, alternate constructions and equivalents may be employed without departing from the true spirit and scope of the invention. For example, in the embodiment where a single reflection occurs in the second deflector, rather than using an idler gear, a belt or chain drive may be used to transmit rotation about the coupler axis to a rotation about the camera axis. This would provide "zero" gear interfaces, an even number. Similarly, while discrete mirror surfaces have been shown, pentaprisms or similar devices could also be used. Moreover, it is possible, although generally not practical to use a total number of reflections that is odd and to compensate for the change in image parity by electronic means within camera control 42. Furthermore, while the description is couched in terms of a television camera, other image receiving means (e.g. movie camera) could also be used if desired. In fact, the coupler of the present invention will compensate for image rotation when inserted between any first optical system and any second optical system where these first or second optical systems themselves may contain optical couplers as described herein. Therefore, the above description and illustrations should not be construed as limiting the scope of the invention which is defined by the appended claims.

I claim:

1. An articulated coupling for transmitting optical information between an endoscope and an image receiving means, the endoscope having a first optical axis, the endoscope being capable of roll rotation about a roll axis parallel to said first optical axis pitch rotation about a pitch axis that is horizontal and perpendicular to the endoscope axis, and yaw rotation about a yaw axis perpendicular to said pitch and roll axes, the image receiving means having a second optical axis that is normally vertical, comprising:

first deflection means for deflecting light travelling along said first optical axis through a right angle about said yaw axis to emerge along a third optical axis that it parallel to said pitch axis;

second deflection means for deflecting light travelling along said third optical axis to emerge along said second optical axis;

first rotatable bearing means between said first and second deflection means to permit relative rotation of said first and second deflection means about said third optical axis;

second rotatable bearing means between said second deflection means and said image receiving means to permit relative rotation of said second deflection means and said image receiving means about said second optical axis; and compensation means responsive to relative rotation between said first and second deflection means about said third optical axis for rotating said image receiving means about said second optical axis relative to said second deflection means such that image rotation due to rotation of said endoscope about said pitch axis is compensated by said rotation of said image receiving means relative to said second deflection means.

2. The invention of claim 1 wherein said second deflection means comprises means for causing said light travelling along said third optical axis to undergo an even number of reflections, and wherein said compensation means comprises gear means defining an odd number of gear interfaces for causing said image receiving means to rotate relative to said second deflection means by an absolute amount equal to the amount of relative rotation between said first and second deflection means.

3. The invention of claim 2 wherein said second deflection means comprises means defining first and second reflective surfaces having an included angle therebetween of 45° and having respective normals lying in the plane defined by said second and third optical axes.

4. The invention of claim 2 wherein said first deflection means comprises means for causing said light travelling along said first optical axis to underto an even number of reflections whereby said optical information arriving at said image receiving means has the same handedness as at said endoscope.

5. The invention of claim 2 wherein said first rotatable bearing means, said second rotatable bearing means, and said gear means together comprise:

a first hollow sleeve bearing rigidly mounted to said second deflection means coaxially with said third optical axis;

a second hollow sleeve bearing rigidly mounted to said second deflection means and aligned coaxially with said second optical axis;

a first bevel gear rigidly coupled to said first deflection means and carried rotatably on said first sleeve bearing; and a second bevel gear rigidly coupled to said image receiving means and carried rotatably on said second sleeve bearing, said first and second bevel gears being mutually engaged for transmitting equal amounts of rotation at right angles to one another.

6. The invention of claim 1 wherein said first deflection means comprises means for transmitting a portion of said light travelling along said first optical axis for direct viewing.

7. The invention of claim 1 wherein said second deflection means comprises means for causing said light travelling along said third optical axis to undergo an odd number of reflections, and wherein said compensation means comprises gear means defining an even number of gear interfaces for causing said image receiving means to rotate relative to said second deflection means by an absolute amount equal to the amount of relative rotation between said first and second deflection means.

8. The invention of claim 7 wherein said first rotatable bearing means, said second rotatable bearing means, and said gear means together comprise:

a first hollow sleeve bearing rigidly mounted to said second deflection means coaxially with said third optical axis;

a second hollow sleeve bearing rigidly mounted to said second deflection means and aligned coaxially with said second optical axis;

a first bevel gear rigidly coupled to said first deflection means and carried rotatably on said first sleeve bearing;

a second bevel gear rigidly coupled to said image receiving means and carried rotatably on said second sleeve bearing;

a third bevel gear; and means for rotatably mounting said third bevel gear to said second deflection means in a position in which said third bevel gear engages said first and second bevel gears to transmit motion between said first and second bevel gears.

9. An articulated coupling for receiving optical information incident along a first optical axis from a first optical system and transmitting said optical information along a second optical axis to a second optical system comprising:

first deflection means for deflecting light travelling along said first optical axis through a right angle to emerge along a third optical axis;

second deflection means for deflecting light travelling along said third optical axis to emerge along said second optical axis;

first rotatable bearing means between said first and second deflection means to permit relative rotation of said first and second deflection means about said third optical axis;

second rotation bearing means between said second deflection means and said second optical system to permit relative rotation of said second deflection means and said second optical system about said second optical axis; and compensation means responsive to relative rotation between said first and second deflection means about said third optical axis for rotating said second optical system about said second optical axis relative to said second deflection means such that image rotation due to relative rotation between said first and second deflection means is compensated by said rotation of said second optical system relative to said second deflection means.

10. The invention of claim 9 wherein said second deflection means comprises means for causing said light travelling along said third optical axis to undergo an even number of reflections, and wherein said compensation means comprises gear means defining an odd number of gear interfaces for causing said image receiving means to rotate relative to said second deflection means by an absolute amount equal to the amount of relative rotation between said first and second deflection means.

11. The invention of claim 10 wherein said second deflection means comprises means defining first and second reflective surfaces having an included angle therebetween of 45° and having respective normals lying in the plane defined by said second and third optical axes.

12. The invention of claim 10 wherein said first deflection means comprises means for causing said light travelling along said first optical axis to underto an even number of reflections whereby said optical information transmitted along said second optical axis has the same handedness as said optical information received along said first optical axis.

13. The invention of claim 10 wherein said first rotatable bearing means, said second rotatable bearing means, and said gear means together comprise:

a first hollow sleeve bearing rigidly mounted to said second deflection means coaxially with said third optical axis;

a second hollow sleeve bearing rigidly mounted to said second deflection means and aligned coaxially with said second optical axis;

a first bevel gear rigidly coupled to said first deflection means and carried rotatably on said first sleeve bearing; and a second bevel gear rigidly coupled to said second optical system and carried rotatably on said second sleeve bearing, said first and second bevel gears being mutually engaged for transmitting equal amounts of rotation at right angles to one another.

14. The invention of claim 9 wherein said first deflection means comprises means for transmitting a portion of said light travelling along said first optical axis for direct viewing.

15. The invention of claim 9 wherein said second deflection means comprises means for causing said light travelling along said third optical axis to undergo an odd number of reflections, and wherein said compensation means comprises gear means defining an even number of gear interfaces for causing said second optical system to rotate relative to said second deflection means by an absolute amount equal to the amount of relative rotation between said first and second deflection means.

16. The invention of claim 15 wherein said first rotatable bearing means, said second rotatable bearing means, and said gear means together comprise:

a first hollow sleeve bearing rigidly mounted to said second deflection means coaxially with said third optical axis;

a second hollow sleeve bearing rigidly mounted to said second deflection means and aligned coaxially with said second optical axis;

a first bevel gear rigidly coupled to said first deflecton means and carried rotatably on said first sleeve bearing;

a second bevel gear rigidly coupled to said second optical system and carried rotatably on said second sleeve bearing;

a third bevel gear; and means for rotatably mounting said third bevel gear to said second deflection means in a position in which said third bevel gear engages said first and second bevel gears to transmit motion between said first and second bevel gears.

* * * * *

UNITED STATES PATENT AND TRADEMARK OFFICE

CERTIFICATE OF CORRECTION

PATENT NO. : 4,248,213

DATED : Feb. 3, 1981

INVENTOR(S) : John K. Landre, La Honda, Calif.

It is certified that error appears in the above-identified patent and that said Letters Patent are hereby corrected as shown below:

Column 9, line 28 should read as follows:

second rotatable bearing means between said second

Signed and Sealed this

*Twenty-eighth* Day of *April 1981*

[SEAL]

*Attest:*

RENE D. TEGTMEYER

*Attesting Officer* *Acting Commissioner of Patents and Trademarks*